United States Patent [19]
Lockard et al.

[11] Patent Number: 5,349,962
[45] Date of Patent: Sep. 27, 1994

[54] METHOD AND APPARATUS FOR DETECTING EPILEPTIC SEIZURES

[75] Inventors: Joan S. Lockard, Bellevue; Larry L. DuCharme, Seattle; William C. Congdon, Jr., Woodinville; Douglas F. Kalk, Seattle, all of Wash.

[73] Assignee: University of Washington, Seattle, Wash.

[21] Appl. No.: 159,855

[22] Filed: Nov. 30, 1993

[51] Int. Cl.⁵ .................. A61B 5/0476; A61B 5/0488
[52] U.S. Cl. ................................. 128/732; 128/731; 128/733
[58] Field of Search ..................... 128/731.3

[56] References Cited

U.S. PATENT DOCUMENTS

| | | | |
|---|---|---|---|
| 3,774,593 | 11/1973 | Hakata et al. | 128/731 |
| 3,850,161 | 11/1974 | Liss | 128/731 |
| 3,863,625 | 2/1975 | Viglione et al. | 128/732 |
| 3,993,046 | 11/1976 | Fernandez et al. | 128/732 |
| 4,873,981 | 10/1989 | Abrams et al. | 128/731 X |

OTHER PUBLICATIONS

Joan S. Lockard, Ph.D. and Ronald I. Barensten, E. E. *Behavioral Experimental Epilepsy in Monkeys. I. Clinical Seizure Recording Apparatus and Initial Data* (Nov. 25, 1966).

Ronald I. Barensten, E. E. and Joan S. Lockard, Ph.D. *Behavioral Experimental Epilepsy in Monkeys. II. Video-Tape Control Gate for the Detection and Recording of Motor Seizures* (Nov. 18, 1968).

Joan S. Lockard, René H. Levy, Indravadan H. Patel, Larry L. DuCharme, and William C. Congdon *Dipropylacetic Acid and Ethosuximide in Monkey Model: Quantitative Methods of Evaluation* (1976).

Joan S. Lockard *A Primate Model of Clinical Epilepsy: Mechanisms of Action Through Quantification of Therapeutic Effects* (1980).

Joan S. Lockard *Social Primate Model of Epilepsy* (1980).

Joan S. Lockard, William C. Congdon, Larry L. DuCharme, and Carin A. Finch *Slow-Speed EEG for Chronic Monitoring of Clinical Seizures in Monkey Model* (1980).

Francesco Pierelli, Gian-Emilio Chatrian, William W. Erdly, and Phillip D. Swanson *Long-Term EEG-Video-Audio Monitoring: Detection of Partial Epileptic Seizures and Psychogenic Episodes by 24-Hour EEG Record Review* (1989).

Flavia Pauri, Francesco Pierelli, Gian-Emilio Chatrian, and William W. Erdly *Long-Term EEG-Video-Audio Monitoring: Computer Detection of Focal EEG Seizure Patterns* (1992).

*Primary Examiner*—Angela D. Sykes
*Attorney, Agent, or Firm*—Christensen, O'Connor, Johnson & Kindness

[57] ABSTRACT

A method and apparatus for accurately determining the onset or occurrence of an epileptic seizure is disclosed. The system includes an electroencephalograph (EEG) and an electromyograph (EMG) which provide signals to a signal processor. The signal processor operates to generate a digitized envelope waveform of the EEG waveform and the EMG waveform. If the waveforms all have an amplitude within a predetermined threshold, for a predetermined time interval, a CPU provides a signal to an output display indicative of a epileptic seizure.

30 Claims, 9 Drawing Sheets

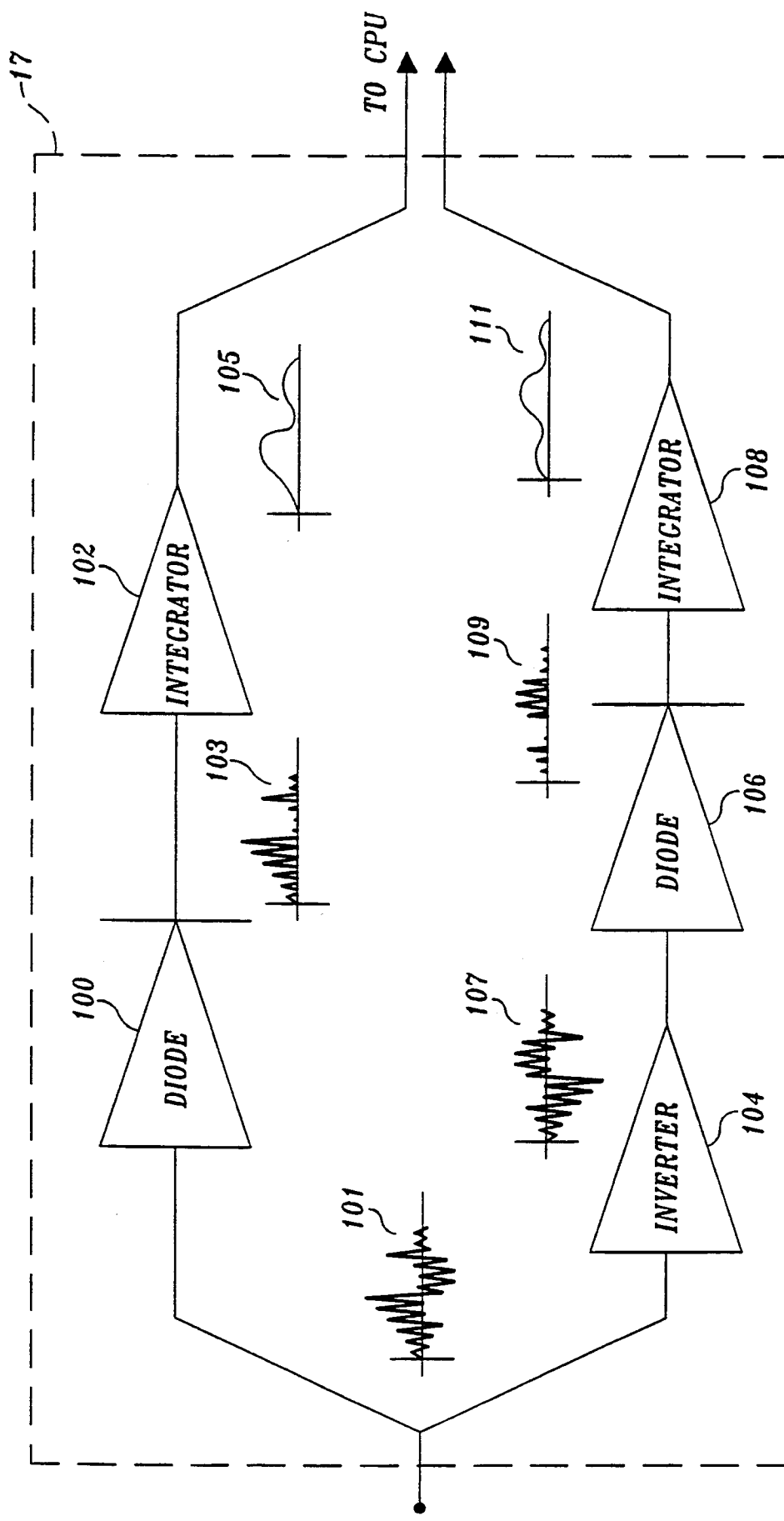

METHOD AND APPARATUS FOR DETECTING EPILEPTIC SEIZURES

FIELD OF THE INVENTION

The present invention relates to monitoring epileptic seizure activity and, more particularly, to a method and apparatus for accurately detecting epileptic seizure activity in a human.

BACKGROUND OF THE INVENTION

Epilepsy is defined as a disorder characterized by recurring seizures, typically manifested by motor, sensory, and/or cognitive malfunction with or without unconsciousness. Motor convulsions are the most common symptom that arises from epilepsy. Convulsive motor attacks can be highly disruptive to normal every day life. Another major category of seizures is the absence seizure, which is a seizure of the brain with little obvious motor movement in its purest form. The occurrence of a seizure with a motor and/or an absence component can be monitored in two ways.

First, the gross motor activity of the patient is typically measured by an electromyograph (EMG) to provide an EMG waveform. An electromyograph operates by monitoring the electrical response of a muscle, in the form of a voltage, to movement. A record of these voltage variations, the EMG waveform, is taken over time. EMG waveforms are made using a mechanical EMG recorder that employs pens to record the analog voltage fluctuations on a strip of paper. As a continuous chart of paper is moved beneath an array of galvanometer driven ink pens, the pens trace out the muscle activity as a series of wavy or jagged lines.

The motor seizure is also typically accompanied by heightened brain activity and thus, an electroencephalograph (EEG) may be used to monitor the seizure by providing an EEG waveform. Further, because the EEG measures brain activity, the EEG can also be used to monitor absence seizures. Similar to an EMG, an EEG monitors brain activity by measuring the very small voltage fluctuations that are generated in the brain, which are detected by electrodes typically attached to a patient's scalp. To aid in studying these analog signals, a record of the voltage fluctuations, the EEG waveform, is often made over time. Traditionally, EEG waveforms are made using a mechanical EEG recorder that employs pens to record the analog voltage fluctuations on a strip of paper. As a continuous chart of paper is moved beneath an array of galvanometer-driven ink pens, the pens trace out the brainwave activity as a series of wavy or jagged lines.

Recently, digital EEGs and EMGs have been developed. Instead of printing the EEG waveforms or EMG waveforms on paper, digital recorders convert sensed analog waveforms into digital signals that are stored in some digital storage medium such as random access memory. (RAM), hard disks, storage tapes, etc. The stored digital waveforms can then be transferred to a digital reader for display and analysis by medical personnel. A digital reader can consist of a personal computer including memory, a processor, input devices and an electronic display screen, e.g., a cathode ray tube (CRT) monitor, for displaying the waveforms.

The information provided by EEGs and EMGs have been used in the prior art to determine if a seizure has taken place or is in progress. However, to date, these methods have proved to be less than convenient or cost effective for daily monitoring. It can be appreciated that it is important to be able to determine when a seizure has occurred, and, by early detection of the onset of a seizure, prevent the seizure. The present invention describes a method and apparatus for detecting seizures in epileptics.

SUMMARY OF THE INVENTION

In accordance with this invention, a method and apparatus for accurately determining the onset or occurrence of an epileptic seizure are provided. The brain activity and the motor activity present in a patient is monitored and brain activity and motor activity signals representing the monitored activities are produced. The brain activity signal is continuously sampled to determine the amplitude of the brain activity signal and the motor activity signal is sampled to determine the amplitude of the motor activity signal. When the brain activity signal amplitude is within a predetermined brain window, a brain activity counter is incremented. When the brain activity signal amplitude is outside the predetermined brain window, the brain activity counter is decremented. Similarly, when the motor activity signal amplitude is within a predetermined motor window, a motor activity counter is incremented. When the motor activity signal amplitude is outside the predetermined motor window, the motor activity counter is decremented. An epileptic seizure is indicated when both the brain activity counter value lies above a brain threshold and the motor activity counter value lies above a motor threshold.

In accordance with other aspects of the present invention, the brain activity signal is provided by an electroencephalograph (EEG) and the motor activity signal is provided by an electromyograph (EMG).

In accordance with other aspects of the present invention, the monitoring of the motor activity signal is separate from the monitoring of the brain activity signal. In this instance, when the motor activity signal amplitude is within a predetermined motor window, a motor activity counter is incremented. When the motor activity signal amplitude is outside the predetermined motor window, the motor activity counter is decremented. An epileptic seizure is indicated when the motor activity counter value lies above a motor threshold.

In accordance with other aspects of the present invention, the monitoring of the brain activity signal is separate from the monitoring of the motor activity signal. In this instance, when the brain activity signal amplitude is within a predetermined brain window, a brain activity counter is incremented. When the brain activity signal amplitude is outside the predetermined brain window, the brain activity counter is decremented. An epileptic seizure is indicated when the brain activity counter value lies above a brain threshold.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein:

FIG. 4 is a schematic diagram of a signal processor suitable for use in the system illustrated in FIG. 1.

DETAILED DESCRIPTION OF THE PREFERRED EMBODIMENT

Figure 1:
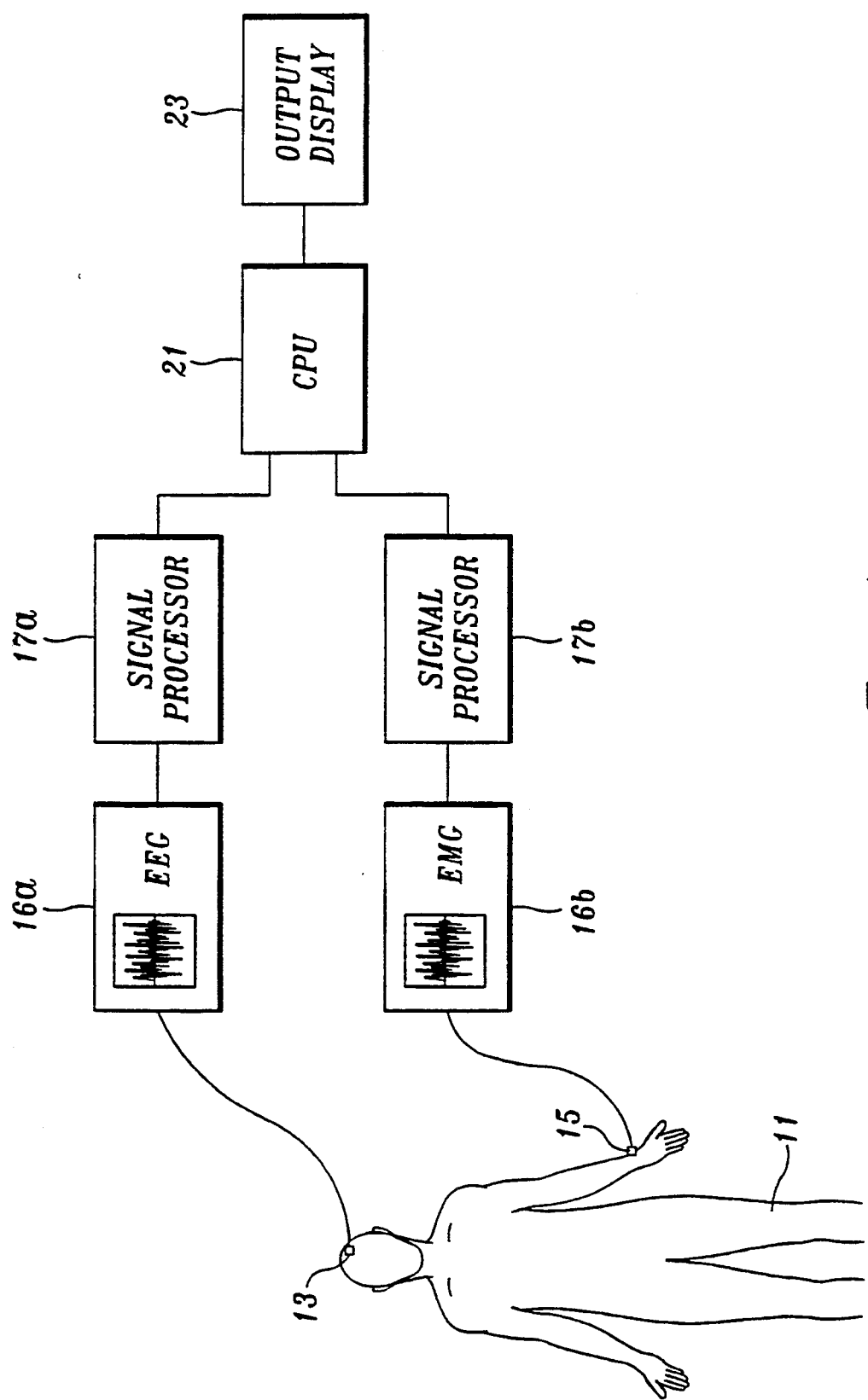
FIG. 1 is an illustration of a system for detecting epileptic seizures formed in accordance with the present invention.

The apparatus formed in accordance with the present invention for detecting epileptic seizures is shown in FIG. 1, which includes a patient 11 being monitored by an EEG sensor 13 and an EMG sensor 15. The remainder of the apparatus includes a slow speed single channel EEG 16a, a slow speed single channel EMG 16b, signal processor 17a and 17b, CPU 21, and output display 23. The EEG sensor 13 is attached to the head of patient 11 and is operative to provide an electrical signal to the EEG 16a that is indicative of the electrical activity in the brain of the patient 11. Similarly, the EMG sensor 15 is attached to the arm of patient 11 and is operative to provide an electrical signal to the EMG 16b that is indicative of the motor activity of the patient 11.

It should be noted that the EMG sensor 15 provides an electrical signal indicative of the activity only in that muscle that is adjacent to the location of the EMG sensor 15. As shown in FIG. 1, the EMG sensor 15 and the EMG 16b monitor the muscles in the arm of the patient 11. In order to monitor the motor activity of other muscles, the EMG sensor must be disposed proximate to those muscles.

While, in the preferred embodiment, an EMG sensor is used to monitor patient motor activity, within the spirit and scope of the present invention, other apparatus can also be used to monitor motor activity. For example, turning to FIG. 1A, an accelerometer sensor 20 may be attached to pans of the patient to measure motor activity. Even though an accelerometer sensor 20 measures the acceleration of the body part to which the sensor is attached, and not electrical activity, an accelerometer sensor 20 will provide a signal that is indicative of motor activity that is suitable for use by the present invention. The signal from the accelerometer sensor 20 is provided to an accelerometer monitor 22. In essence, any apparatus that provides a measure of motor activity may be used in the present invention. Similarly, although the preferred embodiment of the present invention uses an EEG to monitor brain activity, other apparatus that provides a measure of brain activity may also be used.

Figure 1A:
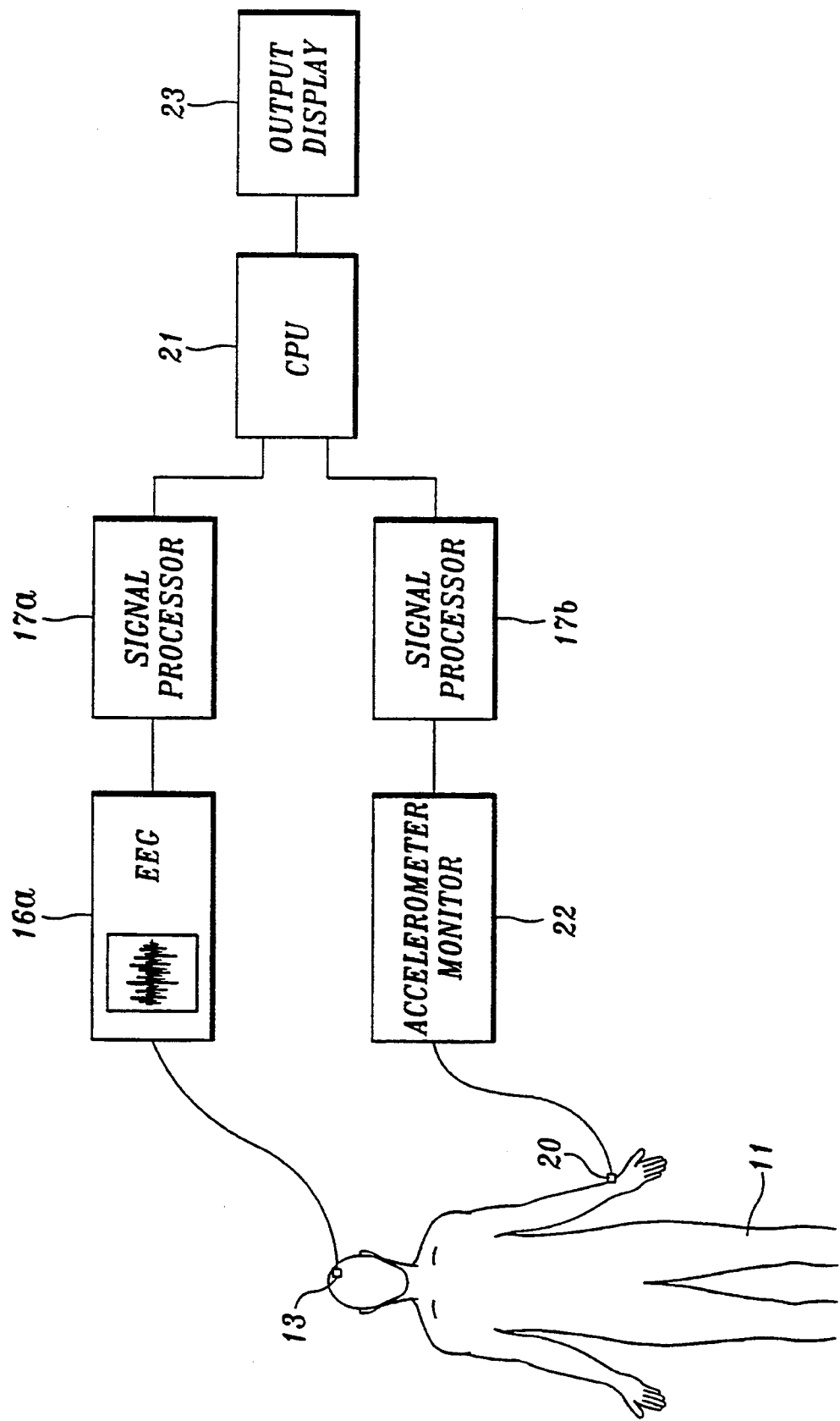
FIG. 1A is an illustration of an alternative embodiment of a system for detecting epileptic seizures formed in accordance with the present invention.

While FIG. 1A illustrates an alternative embodiment of the present invention where the means for monitoring the motor activity of the patient is an accelerometer sensor 20 and an accelerometer monitor 22, all other aspects of the alternative embodiment shown in FIG. 1A are identical to the preferred embodiment shown in FIG. 1. Thus, the remaining elements of FIG. 1A are not discussed further.

Returning to FIG. 1, the signals monitored by the sensors 13 and 15 are provided to the EEG 16a and the EMG 16b, respectively. The EEG 16a processes the electrical signals generated by the EEG sensor 13 into analog fore suitable for displaying on a continuous stream of paper or a CRT. Similarly, the EMG 16b processes the electrical signals generated by the EMG sensor 15 into analog form suitable for displaying on a continuous stream of paper or a CRT. In accordance with the invention, the analog waveforms produced by the EEG 16a and EMG 16b are each applied to a signal processor 17a and 17b. For purposes of explanation, representations of the waveform output of the EEG 16a and the EMG 16b are shown in FIGS. 2A and 2B, respectively.

Figure 2A:
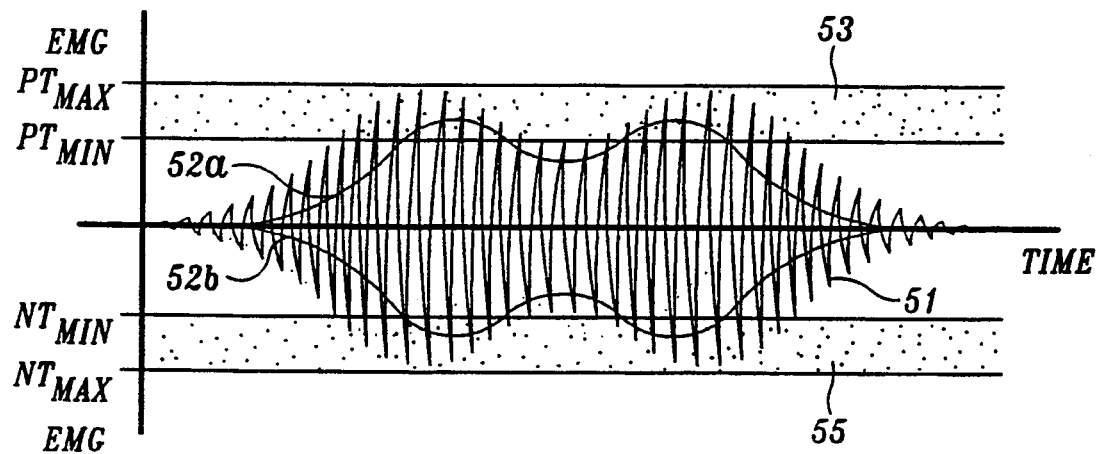
FIGS. 2A–B are examples of waveforms produced by EMG and EEG monitors.
Figure 2B:
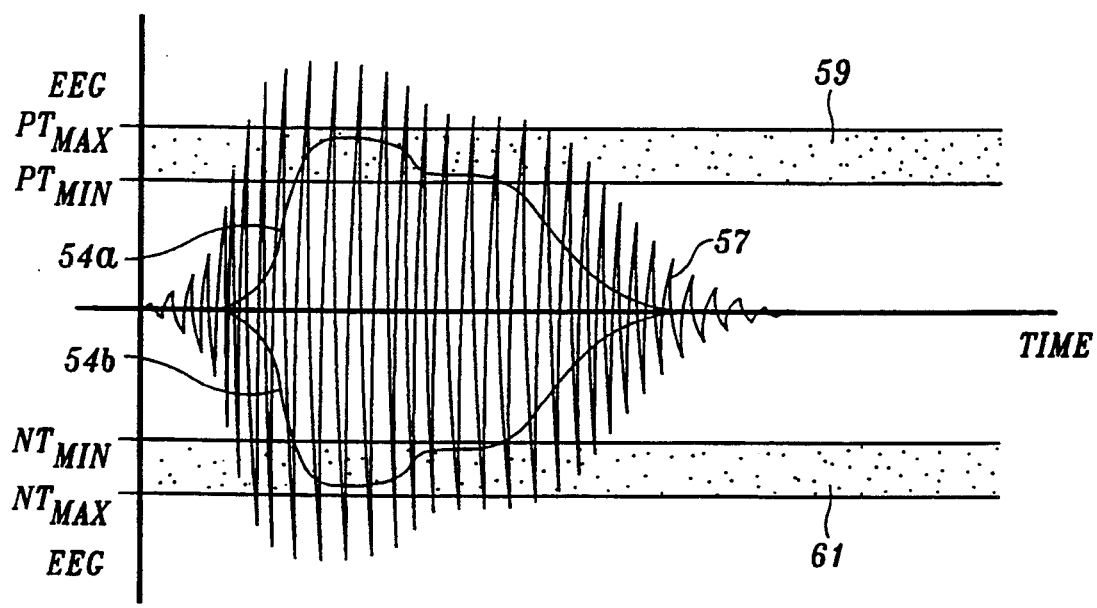

As seen in FIGS. 2A–2B, the EEG waveform and the EMG waveform are charted with time progressing on the x-axis and amplitude charted on the y-axis. The amplitude is a measure of the voltage provided by the sensors 13 and 15. As will be appreciated by those skilled in the art, the EEG and EMG waveforms will invariably oscillate about the x-axis. In particular, FIG. 2A shows an EMG waveform 51. The waveform indicates that the patient 11 is experiencing a steady increase of muscle activity, followed by a slight dip, followed by a rise in activity, and concluding with a steadily decreasing period of muscle activity. This EMG waveform is typical of the type of waveform generated by a person undergoing a seizure. Similarly, FIG. 2B shows an EEG waveform 57. The waveform indicates that the patient 11 is experiencing a rapid increase of brain activity, followed by a plateau period, followed by a decrease to a second plateau, and concluding with a steadily decreasing period of brain activity.

As stated above, the outputs of the EEG 16a and the EMG 16b are each applied to a separate signal processor 17a and 17b. FIG. 4 is a more detailed diagram of the processing circuitry included in the signal processors 17a and 17b. Since the construction of both of the signal processors 17a and 17b is identical, only a description of the signal processor 17a associated with the EEG 16a is provided herein. Signal processor 17a includes two diodes 100 and 106, an inverter 104, and two integrators 102 and 108. The signal from the EEG 16a enters at the left hand side of FIG. 4 and is applied to one of the diodes 100 and to the inverter 104. An example of a typical signal from the EEG 16a is shown by the waveform identified by reference number 101.

Following first the upper branch of the processing circuitry, the diode 100 only allows the positive portion of the input signal to be passed. The negative portion of the waveform input into diode 100 is eliminated by the diode. The output signal of the diode 100 is shown by the waveform identified by reference number 103. For purposes of description, the upper branch of the signal processor 17a is also referred to herein as the positive signal branch.

Next, the signal shown by waveform reference number 103 is input into one of the integrators 102 which integrates the signal. By integration, it is meant that an "envelope waveform" is generated which generally follows the amplitude of the signal. Since envelope integrations are well known to those of ordinary skill in the electronic art, a specific integration is not described here. The output of integrator 102, shown by the waveform identified by reference numeral 105, is applied by the signal processor 17a to the CPU 21 in real time. The output signal of the integrator 102, which is the output of the positive signal branch of the processor 17a, is herein referred to as the positive EEG envelope waveform. Similarly, in the case of the signal processor 17b associated with the EMG 16b, the integrator in the positive signal branch generates a positive EMG envelope waveform.

Turning now to the lower, or negative signal, branch of the processing circuitry, the EEG waveform 101 is first applied to the inverter 104. The inverter 104 changes the sign, or polarity, of the signal. Thus, the EEG waveform 101 is "flipped" about the x-axis. The output of inverter 104 is shown by a waveform identified by reference numeral 107. The inverted signal 107 is applied to the other diode 106, which passes only the positive portion of the signal. Because the signal has been inverted, the positive portion of the signal is the negative portion of the EEG waveform input to the signal processor 17a and shown as reference numeral 101. The output signal from diode 106 is shown by the waveform identified by reference number 109.

Next, the signal shown by waveform reference number 109 is input into an integrator 108, which integrates the signal. Again, the integrator performs an envelope integration, i.e., the integrator produces an "envelope waveform" that substantially follows the amplitude of the input signal. The output of integrator 108, which is a waveform identified by reference numeral 111, is applied by the signal processor 17a to the CPU 21 in real time. The output signal of the integrator 108, which is the output of the negative signal branch of processor 17a, is referred to as the negative EEG envelope waveform. Similarly, in the case of the signal processor 17b associated with the EMG 16a, the integrator in the negative signal branch generates a negative EMG envelope waveform.

To further illustrate, positive EMG envelope waveform 52a and negative EMG envelope waveform 52b are also shown in FIG. 2A; and positive EEG envelope waveform 54a and negative EEG envelope waveform 54b are shown in FIG. 2B. While, as shown in FIGS. 2A and 2B, the envelope waveforms in actual practice are often times symmetrical about the x-axis, the envelope waveforms may from time to time be asymmetrical, i.e., the negative envelope may not simply be a mirror of the positive envelope.

In summary, the EEG signal processor 17a provides two outputs: a positive EEG envelope waveform 54a and a negative EEG envelope waveform 54b (which has been rectified to appear positive). Further, the EMG signal processor 17b provides two outputs: a positive EMG envelope waveform 52a and a negative EMG envelope waveform 52b (which has been rectified to appear positive). Further, although the signal processors 17a-b have been shown as a combination of diodes, rectifiers, and integrators, it is to be understood that the entire functionality of the signal processors 17a-b can be implemented in other forms, including software. Thus, FIG. 4 should be considered to be illustrative and not limiting.

Figure 3A:
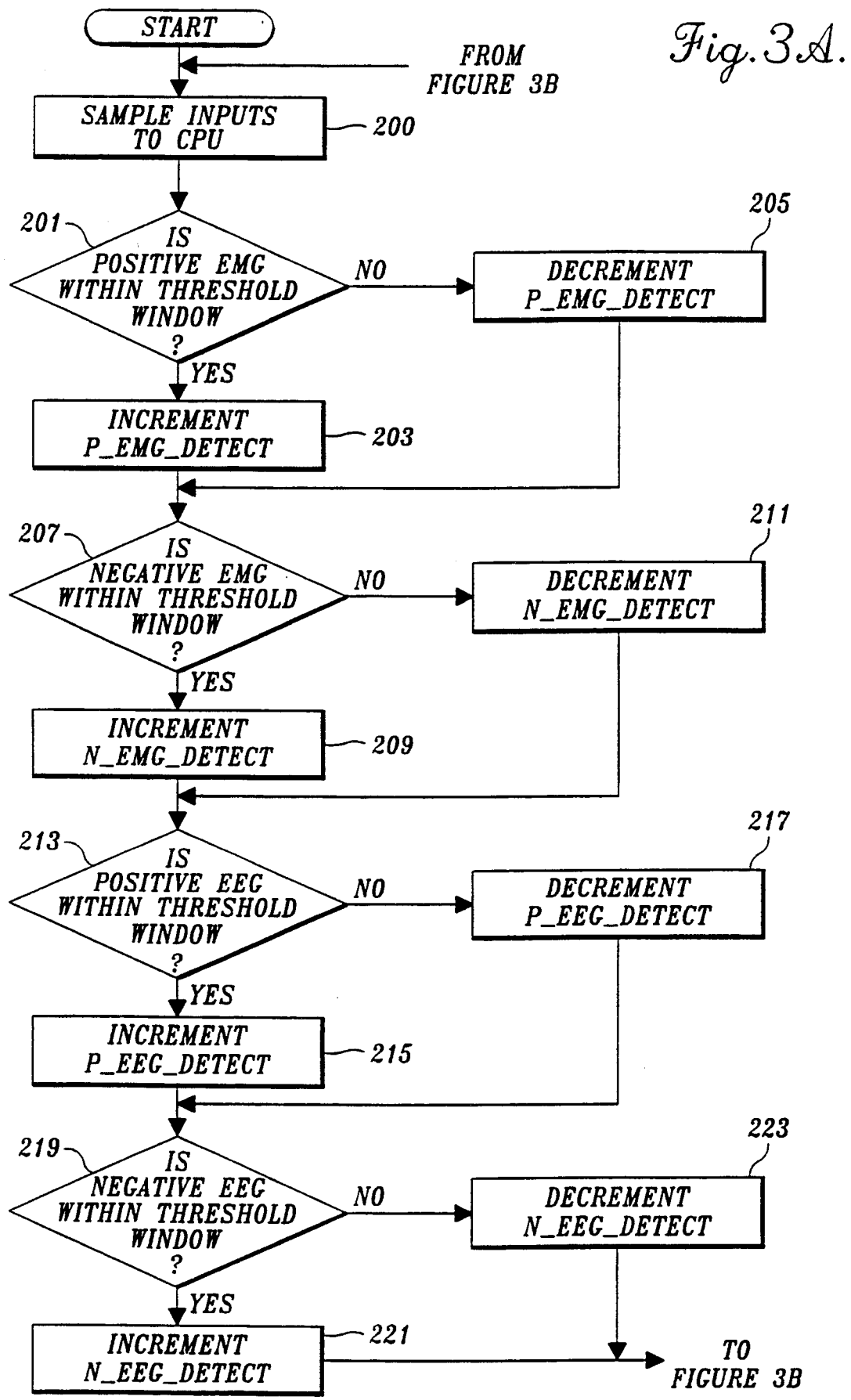
FIGS. 3A–B are flow diagrams illustrating a method of detecting epileptic seizures formed in accordance with the present invention.
Figure 3B:
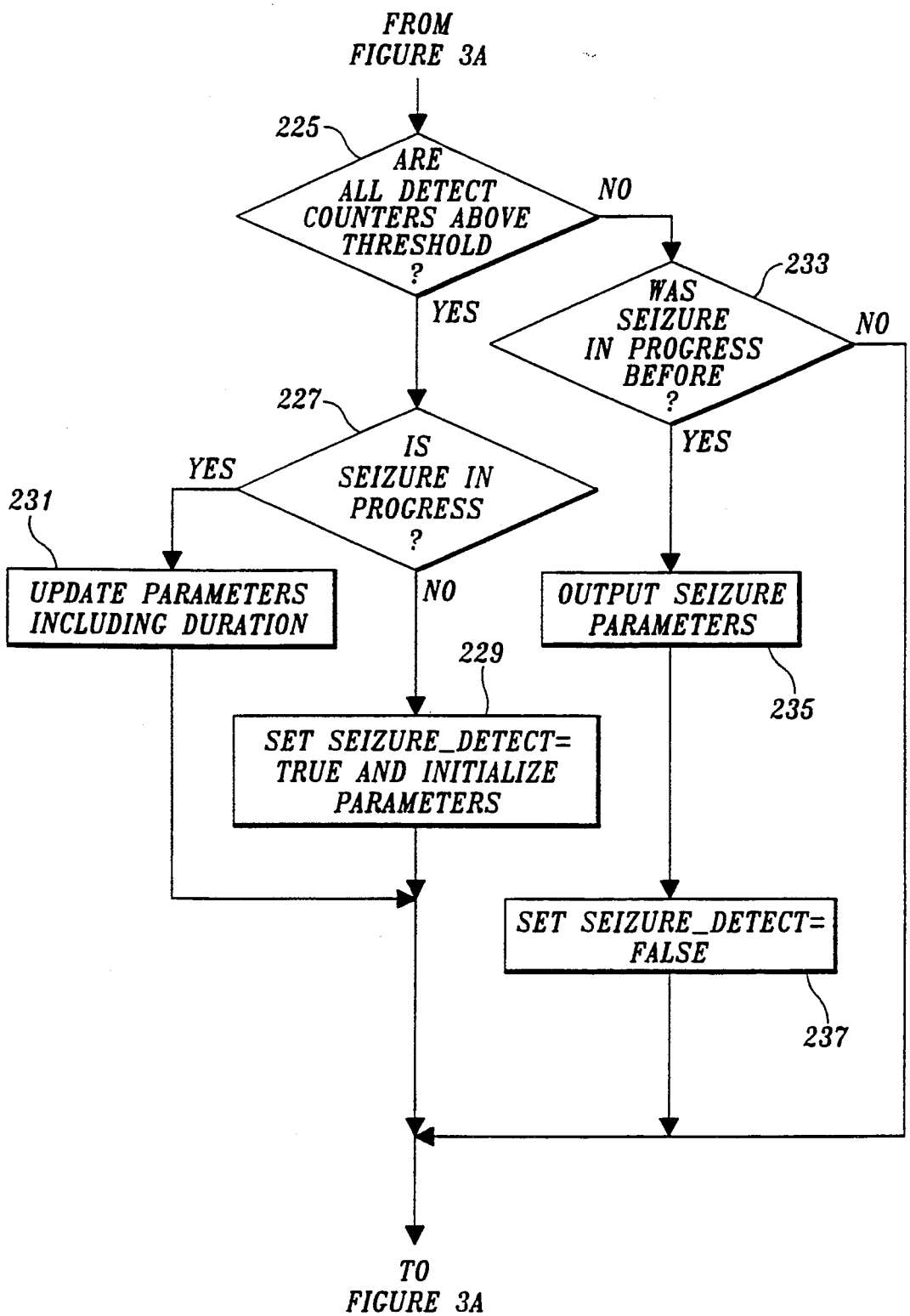

In accordance with this invention, the CPU 21 operates on the waveforms provided by the signal processors 17a and 17b. FIGS. 3A and 3B form a flow diagram that illustrates the preferred method of operation of the CPU 12. First, at box 200, all of the waveform inputs to CPU 21 are sequentially sampled at a particular rate and the results stored in memory registers. As will be seen in greater detail below, the values stored in the memory registers are used to calculate certain seizure parameters. While, preferably, the envelope waveforms are sampled at a rate of ten times per second (10 Hz), it is to be understood that other sampling rates may be used that are higher or lower than 10 Hz.

Next, at box 201, the sampled value of the positive EMG envelope waveform 52a is examined to determine if it falls within a positive threshold window, i.e., above a predetermined minimum positive threshold and below a predetermined maximum positive threshold. FIG. 2A shows the positive threshold window 53 (delineated as $PT_{max}$ and $PT_{min}$) superimposed over the positive EMG envelope waveform 52a. The predetermined minimum and maximum thresholds that define the positive threshold window 53 are stored in CPU 21. Typically, these threshold values are empirically determined. Oftentimes, the threshold values change from patient to patient. Thus, the apparatus of the present invention can be "calibrated" to suit an individual patient.

If the amplitude of the sampled value of the positive EMG envelope waveform 52a is within the window, then at box 203, a counter maintained in CPU 21 designated as P_EMG_DETECT is incremented. While the amount of the incrementation is typically one for some patients, the amount of incrementation may be greater than one. As will be seen in greater detail below, in the preferred embodiment of the present invention, the apparatus will not indicate that a seizure is in progress until the value of the P_EMG_DETECT counter reaches a predetermined value. For more sensitive patients, it may be necessary to increment the P_EMG_DETECT counter at a higher step rate in order to more readily detect seizures. Alternatively, for less sensitive patients, it may be necessary to increment the P_EMG_DETECT counter at a lower step rate. Further, when the P_EMG_DETECT counter reaches a predetermined maximum, designated as P_EMG_DETECT_MAX, the P_EMG_DETECT counter is not incremented further. Rather, the counter is maintained at the predetermined maximum P_EMG_DETECT_MAX.

If the amplitude of the sampled value of the positive EMG envelope waveform 52a is not within the window, then at box 205, the P_EMG_DETECT counter is decremented. Like incrementing the P_EMG_DETECT counter, the amount of decrementation may vary and may be adjusted to suit a particular patient. Also, when the counter reaches a predetermined minimum, designated as P_EMG_DETECT_MIN, the counter is not further decremented.

A similar analysis is performed by CPU 21 on the amplitude of the negative EMG envelope waveform 52b. At box 207 the amplitude of the sampled value of the negative EMG envelope waveform 52b is examined to determine if it falls within a negative threshold window, i.e., below a predetermined minimum negative threshold and above a predetermined maximum negative threshold. FIG. 2A shows the negative threshold window 55 (delineated as $NT_{max}$ and $NT_{min}$) superimposed over the negative EEG envelope waveform 52b. The predetermined minimum and maximum thresholds that form the negative threshold window 55 are stored in CPU 21. As above, these threshold values are empirically determined.

If the amplitude of the sampled value of the negative EMG envelope waveform 52b is within the window, then at box 209, a counter maintained in CPU 21 designated as N_EMG_DETECT is incremented. While the amount of the incrementation is typically one for some patients, the amount of incrementation may be greater than one. In the preferred embodiment of the present invention, the apparatus will not indicate that a seizure is in progress until the value of the N_EMG_DETECT counter reaches a predetermined value. For more sensitive patients, it may be necessary to increment the N_EMG_DETECT counter at a higher step rate in order to more readily detect seizures. Alternatively, for less sensitive patients, it may be necessary to increment the N_EMG_DETECT counter at a lower step rate. Further, when the N_EMG_DETECT counter reaches a predetermined maximum, designated as N_EMG_DETECT_MAX, the N_EMG_DETECT counter is not incremented further.

If the amplitude of the sampled value of the negative EMG envelope waveform 52b is not within the window, then at box 211, the N_EMG_DETECT counter is decremented. Like incrementing the N_EMG_DETECT counter, the amount of decrementation may vary and may be adjusted to suit a particular patient. Also, when the counter reaches a predetermined minimum, designated as N_EMG_DETECT_MIN, the counter is not further decremented.

A similar analysis is performed by CPU 21 on the amplitude of the positive EEG envelope waveform 54a. In particular, at box 213, the amplitude of the sampled value of the positive EEG envelope waveform 54a is examined to determine if it falls within a positive threshold window, i.e., above a predetermined minimum threshold and below a predetermined maximum threshold. FIG. 2B shows the positive threshold window 59 (delineated as $PT_{max}$ and $PT_{min}$) superimposed over the positive EEG envelope waveform 54a. The predetermined minimum and maximum thresholds that form the window 59 are stored in CPU 21. Typically, these threshold values are empirically determined.

If the amplitude of the sampled value of the positive EEG envelope waveform 54a is within the window, then at box 215, a counter maintained in CPU 21 designated as P_EEG_DETECT is incremented. While the amount of incrementation is typically one for some patients, the amount of incrementation may be greater than one. As will be seen in greater detail below, in the preferred embodiment of the present invention, the apparatus will not indicate that a seizure is in progress until the value of the P_EEG_DETECT counter reaches a predetermined value. For more sensitive patients, it may be necessary to increment the P_EEG_DETECT counter at a higher step rate in order to more readily detect seizures. Alternatively, for less sensitive patients, it may be necessary to increment the P_EEG_DETECT counter at a lower step rate. Further, when the P_EEG_DETECT counter reaches a predetermined maximum, designated as P_EEG_DETECT_MAX, the P_EEG_DETECT counter is not incremented further.

If the amplitude of the sampled value of the positive EEG envelope waveform 54a is not within the window, then at box 217, the P_EEG_DETECT counter is decremented. Like incrementing the P_EEG_DETECT counter, the amount of decrementation may vary and may be adjusted to suit a particular patient. Also, when the counter reaches a predetermined minimum, designated as P_EEG_DETECT_MIN, the counter is not further decremented.

Finally, a similar analysis is performed by CPU 21 on the amplitude of the negative EEG envelope waveform 54b. At box 219 the amplitude of the sampled value of the rectified negative EEG envelope waveform 54b is examined to determine if it falls within a negative threshold window, i.e., below a predetermined minimum threshold and above a predetermined maximum threshold. FIG. 2B shows the negative threshold window 61 (delineated as $NT_{max}$ and $NT_{min}$) superimposed over the negative envelope waveform of the EEG signal 54b. The predetermined minimum and maximum thresholds that form the window 61 are stored in CPU 21. As above, these threshold values are empirically determined.

If the amplitude of the sampled value of the negative EEG envelope waveform 54b is within the window, then at box 221, a counter maintained in CPU 21 designated as N_EEG_DETECT is incremented. While the amount of the incrementation is typically one for some patients, the amount of incrementation may be greater than one. In the preferred embodiment of the present invention, the apparatus will not indicate that a seizure is in progress until the value of the N_EEG_DETECT counter reaches a predetermined value. For more sensitive patients, it may be necessary to increment the N_EEG_DETECT counter at a higher step rate in order to more readily detect seizures. Alternatively, for less sensitive patients, it may be necessary to increment the N_EEG_DETECT counter at a lower step rate. Further, when the counter N_EEG_DETECT is already at a predetermined maximum, designated as N_EEG_DETECT_MAX, the N_EEG_DETECT counter is not incremented further.

If the amplitude of the sampled value of the negative EEG envelope waveform 54b is not within the window, then at box 223, the N_EEG_DETECT counter is decremented. Like incrementing the N_EEG_DETECT counter, the amount of decrementation may vary and may be adjusted to suit a particular patient. Also, when the counter reaches a predetermined minimum, designated as N_EEG_DETECT_MIN, the counter is not decremented further. It can be seen from the above description that several of the parameters are predetermined and can be adjusted to suit a particular individual.

Next, turning to FIG. 3B, at box 225, all of the detect counters (P_EMG_DETECT, N_EMG_DETECT, P_EEG_DETECT, and N_EEG_DETECT) are checked to determine whether they are greater than a predetermined threshold integer number designated as DETECT_THRESH and stored in CPU 21. While preferably DETECT_THRESH is the same number for all of the detect counters, it is to be understood that different thresholds can be used for each of the detect counters.

If all of the detect counters are above DETECT_THRESH, then at step 227, a determination is made as to whether or not a seizure is already in progress. This is done by checking a SEIZURE_DETECT flag stored in CPU 21. The flag can register TRUE or FALSE. Initially, the flag is set to FALSE. It is set to TRUE during a subsequent step of the method illustrated in FIG. 3B, which is described below. If the SEIZURE_DETECT flag is TRUE, a seizure is in progress. In essence, a TRUE setting of the SEIZURE_DETECT flag establish that the signals received from the sensors 15 and 13 indicate that a previously detected seizure is continuing. In such a case, at box 231, certain measurement parameters maintained by CPU 21 are updated.

The updated measurement parameters include the maximum amplitude of the EEG and EMG envelope waveforms as sampled by CPU 21, the average amplitudes of the EEG and EMG envelope waveforms over the seizure period, the time duration of the seizure, and the time at which the seizure started. Recall that each time the CPU 21 samples the output from the signal processors 17A-17B, the sampled values of the waveforms are stored in memory registers of the CPU 21. Thus, it is an easy task to generate the measurement parameters from the stored sampled values. For example, the maximum amplitude of a waveform can be extracted by examining the stored sampled values after each sample. Each time a larger amplitude is detected, the previous maximum amplitude for the EEG or EMG can be replaced therewith. Similarly, the duration of the seizure can be measured using the internal clock of the CPU 21. Finally, the average amplitude can be calculated by examining each of the EEG and EMG samples and calculating an arithmetic average thereof.

If, at box 227, the seizure progress test is negative, i.e. the SEIZURE_DETECT flag is not set, then this means that a new seizure is beginning. In such a case, at box 229, the SEIZURE_DETECT flag is set to TRUE. Further, at box 229, the measurement parameters are initialized. In particular, the time at which the seizure begins is recorded in a memory register of CPU 21. Further, additional memory registers of CPU 21 used to monitor the time duration of the seizure, and record the amplitude maximums and average are cleared. Because the recording of measurement parameters can be implemented by standard software techniques, such techniques are not described in detail here. Following box 229, the CPU returns to box 200 and the cycle repeats.

If, at box 225, the detect counters are not all above the predetermined threshold, then at box 233, a determination is made as to whether or not a seizure was in progress. Once again this is accomplished by examining the SEIZURE_DETECT flag. If a seizure was in progress at box 233, the fact that one or more of the counters has dropped below its threshold indicates that the seizure is concluding. If a seizure was in progress at a box 235, the seizure parameters noted above are output to output display 23 (FIGS. 1 or 1A). Next, at box 237, the SEIZURE_DETECT flag is set to FALSE and the program cycles to box 200. If at box 233, there was no seizure in progress, the CPU simply cycles to box 200 for further monitoring without outputting the seizure parameters.

Figure 3C:
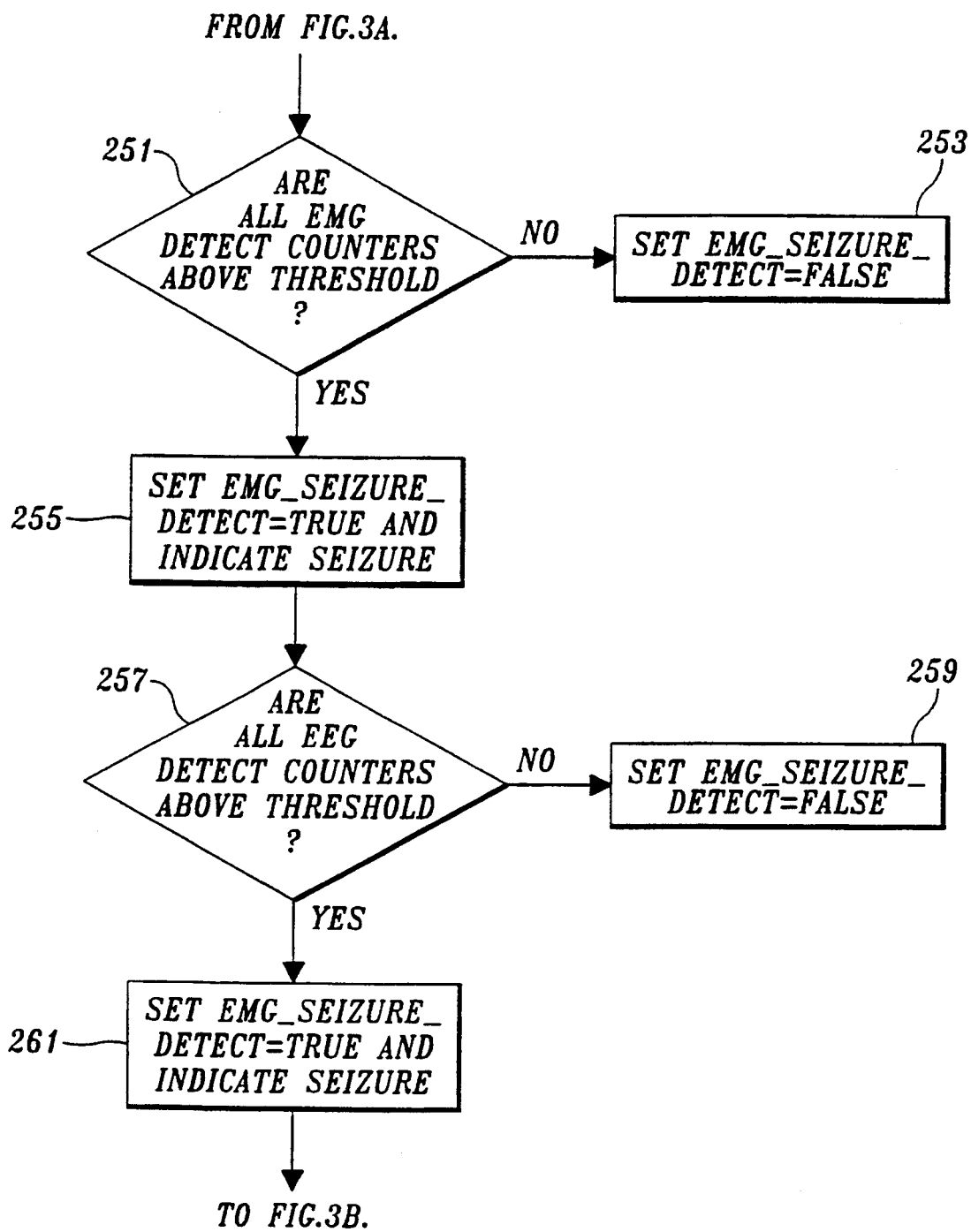
FIG. 3C is a flow diagram illustrating an alternative embodiment of the present invention.

In the above description of the preferred embodiment, all of the detection counters must be above their predetermined thresholds before the apparatus indicates that a seizure has been detected. This is satisfactory for motor seizures. However, absence seizures would not be detected by this method, because little or no motor component is associated with absence seizures. In absence seizures, only EEG waveform activity establishes the occurrence of the absence seizure. Similarly, there are occasions where a seizure may occur with very little brain activity and a high motor component. In those cases, only the EMG waveform activity establishes the occurrence/the seizure. FIG. 3C illustrates an alternative embodiment of the invention directed to covering these variations. The entry into the flow diagram of FIG. 3C is from boxes 223 or 221 from FIG. 3A, i.e., after the sampled values of the envelope waveforms have been examined.

At box 251, a determination is made as to whether the value stored in the P_EMG_DETECT and N_EMG_DETECT counters are greater than a predetermined threshold integer number. If both the detect counters are above the predetermined threshold, then at step 255, a EMG_SEIZURE_DETECT flag is set to TRUE and the output display 23 indicates that an EMG seizure has taken place. If both detect counters are not above the threshold, then at box 253, the EMG_SEIZURE_DETECT flag is set to FALSE. The flag is a binary flag that can register TRUE or FALSE. Initially, the flag is set to FALSE. Setting the EMG_SEIZURE_DETECT flag to TRUE indicates that a seizure is in progress.

Next, at box 257, a determination is made as to whether the values stored in the P_EEG_DETECT and N_EEG_DETECT counters are greater than a predetermined threshold integer number. If both the detect counters are above the predetermined threshold, then at step 261, a EEG_SEIZURE_DETECT flag is set to TRUE and the output display 23 indicates that an EEG seizure has taken place. If both detect counters are not above the threshold, then at box 259, the flag EEG_SEIZURE_DETECT is set to FALSE. The flag is a binary flag that can register TRUE or FALSE. Initially, the flag is set to FALSE. Setting the EEG_SEIZURE_DETECT flag to TRUE, indicates that a seizure is in progress. After box 261, the flow diagram returns to box 200 for further monitoring.

Figure 3D:
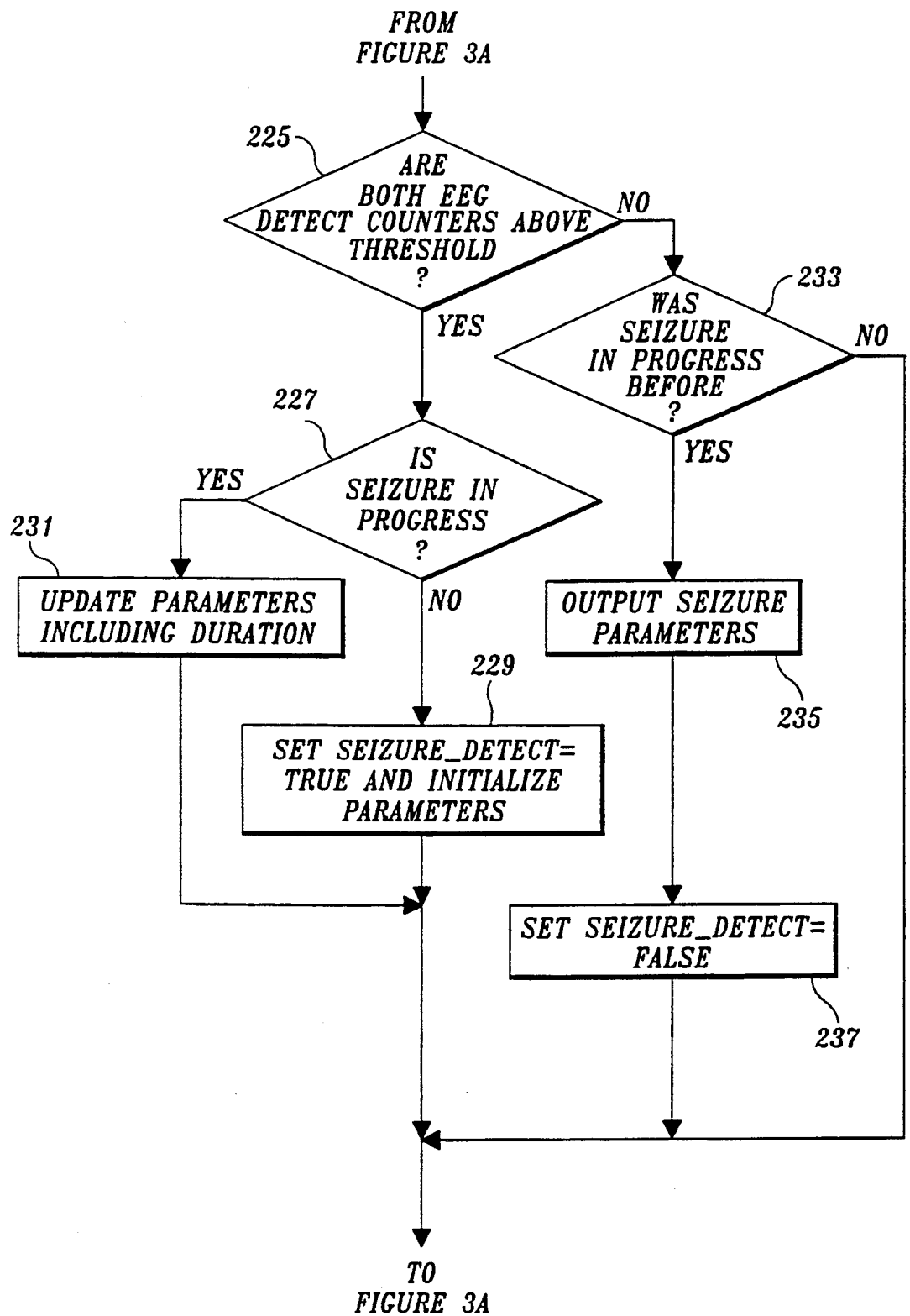
FIGS. 3D–3E are flow diagrams illustrating another alternative embodiment of the present invention.

The alternative embodiment shown in FIG. 3C only provides an indication of whether or not an EMG or EEG seizure has taken place, but not the seizure parameters. The preferred embodiment shown in FIGS. 3A-B can easily be modified so as to output the seizure parameters for an EMG or EEG seizure. In particular, in this second alternative embodiment, as illustrated in the flow diagram in FIG. 3D, the same methodology as used in the preferred embodiment as shown in FIG. 3B is followed, except that at box 225 of FIG. 3B, only the EEG detect counters are examined. In all other respects, FIG. 3D is identical to FIG. 3B.

Figure 3E:
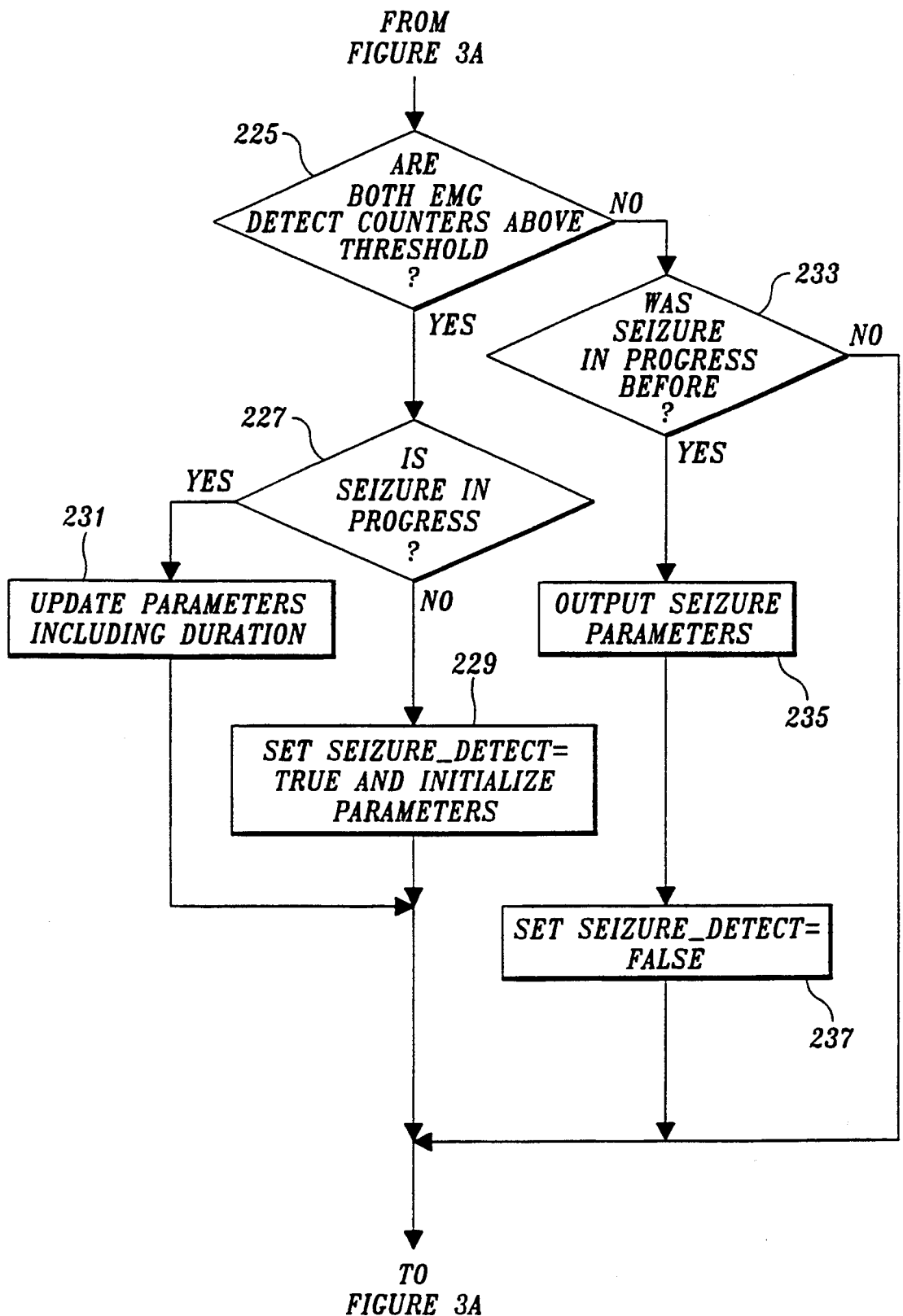

Similarly, as illustrated in the flow diagram in FIG. 3E, the brain activity of a patient can be monitored for absence seizures. In particular, the same methodology as used in the preferred embodiment as shown in FIG. 3B is followed, except that at box 225 of FIG. 3B, only the EMG detect counters are examined. In all other respects, FIG. 3E is identical to FIG. 3B.

While the preferred embodiment of the invention has been illustrated and described, it will be appreciated that various changes can be made therein without departing from the spirit and scope of the invention.

We claim:

1. A method of detecting an epileptic seizure in a person comprising the steps of:
   (a) monitoring the amount of brain activity of said person to produce a brain activity signal and monitoring the amount of motor activity of said person to produce a motor activity signal;
   (b) sampling said brain activity signal at a sampling frequency to produce a brain activity signal amplitude and sampling said motor activity signal at said sampling frequency to produce a motor activity signal amplitude;
   (c) incrementing a brain activity counter when said brain activity signal amplitude is within a predetermined brain window and decrementing said brain activity counter when said brain activity signal is without said predetermined brain window;

(d) incrementing a motor activity counter when said motor activity signal amplitude is within a predetermined motor window and decrementing said motor activity counter when said motor activity signal is without said predetermined motor window; and (e) indicating that an epileptic seizure is occurring when said brain activity counter is above a brain threshold and said motor activity counter is above a motor threshold.

2. The method of claim 1 further including the steps of:
determining the maximum amplitude of said brain activity signal when said brain activity counter is above said brain threshold; and
determining the maximum amplitude of said motor activity signal when said motor activity counter is above said motor threshold.

3. The method of claim 1 further including the steps of:
determining the average amplitude of said brain activity signal over the interval when said brain activity counter is above said brain threshold; and
determining the average amplitude of said motor activity signal over the interval when said motor activity counter is above said motor threshold.

4. The method of claim 1 further including the step of determining the duration of time in which said brain activity counter is above said brain threshold and the said motor activity counter is above said motor threshold.

5. The method of claim 1 wherein the step of monitoring the brain activity of said person is done by means of an electroencephalograph (EEG) and said brain activity signal is an EEG waveform and wherein the step of monitoring the motor activity of said person is done by means of an electromyograph (EMG) and said motor activity signal is an EMG waveform.

6. The method of claim 5 wherein said EEG waveform has a positive EEG component and a negative EEG component and wherein said EMG waveform has a positive EMG component and a negative EMG component, wherein said step of sampling is acted upon said positive EEG component, said negative EEG component, said positive EMG component, and said negative EMG component, further wherein said brain activity counter includes a positive brain activity counter and a negative brain activity counter and wherein said motor activity counter includes a positive motor activity counter and a negative motor activity counter, the method further including the steps of:

(a) integrating said positive EEG component to provide a positive EEG envelope waveform and integrating said negative EEG component to provide a negative EEG envelope waveform;

(b) integrating said positive EMG component to provide a positive EMG envelope waveform and integrating said negative EMG component to provide a negative EMG envelope waveform;

(c) incrementing said positive brain activity counter when said positive EEG envelope waveform is within said predetermined brain window and decrementing said positive brain activity counter when said positive EEG envelope waveform is without said predetermined brain window;

(d) incrementing said negative brain activity counter when said negative EEG envelope waveform is within said predetermined brain window and decrementing said negative brain activity counter when said negative EEG envelope waveform is without said predetermined brain window;

(e) incrementing said positive motor activity counter when said positive EMG envelope waveform is within said predetermined motor window and decrementing said positive motor activity counter when said positive EMG envelope waveform is without said predetermined motor window, and (f) incrementing said negative motor activity counter when said negative EMG envelope waveform is within said predetermined motor window and decrementing said negative motor activity counter when said negative EMG envelope waveform is without said predetermined motor window.

7. A method of detecting an epileptic seizure in a person comprising the steps of:

(a) monitoring the amount of brain activity of said person as to produce a brain activity signal and monitoring the amount of motor activity of said person to produce a motor activity signal;

(b) determining if the amplitude of said brain activity signal falls within a predetermined brain window for a predetermined brain window period and determining if the amplitude of said motor activity signal falls within a predetermined motor window for a predetermined motor window period; and (c) indicating that an epileptic seizure has occurred when said amplitude of said brain activity signal falls within a predetermined brain window for a predetermined brain window period and the amplitude of said motor activity signal falls within a predetermined motor window for a predetermined motor window period.

8. The method of claim 7 further including the steps of:
determining the maximum amplitude of said brain activity signal over the interval said brain activity signal falls within said predetermined brain window; and
determining the maximum amplitude of said motor activity signal over the interval said motor activity signal falls within said predetermined motor window.

9. The method of claim 7 further including the steps of:
determining the average amplitude of said brain activity signal over the interval when said brain activity signal falls within said predetermined brain window; and
determining the average amplitude of said motor activity signal over the interval when said motor activity signal falls within said predetermined motor window.

10. The method of claim 7 further including the step of:
determining the duration of time in which the amplitude of said brain activity signal falls within said predetermined brain window and the amplitude of said motor activity signal falls within said predetermined motor window.

11. The method of claim 7 including wherein the step of monitoring the brain activity of said person is done by means of an electroencephalograph (EEG) and said brain activity signal is an EEG waveform and wherein the step of monitoring the motor activity of said person is done by means of an electromyograph (EMG) and said motor activity signal is an EMG waveform.

12. The method of claim 11 further wherein said EEG waveform has a positive EEG component and a negative EEG component and wherein said EMG waveform has a positive EMG component and a negative EMG component, the method further including the steps of:
   (a) integrating said positive EEG component to provide a positive EEG envelope waveform and integrating said negative EEG component to provide a negative EEG envelope waveform;
   (b) integrating said positive EMG component to provide a positive EMG envelope waveform and integrating said negative EMG component to provide a negative EMG envelope waveform;
   (c) determining whether the amplitude of said positive EEG envelope waveform falls within said predetermined window for said predetermined brain window period and determining whether the amplitude of said negative EEG envelope waveform falls within said predetermined window for said predetermined brain window period;
   (d) determining whether the amplitude of said positive EMG envelope waveform falls within said predetermined window for said predetermined motor window period and determining whether the amplitude of said negative EMG envelope waveform falls within said predetermined window for said predetermined motor window period; and
   (e) indicating that an epileptic seizure has occurred when said amplitude of said positive EEG envelope waveform falls within said predetermined brain window for said predetermined brain window period, when the amplitude of said negative EEG envelope waveform falls within said predetermined brain window for said predetermined brain window period, when the amplitude of said positive EMG envelope waveform falls within said predetermined motor window for said predetermined motor window period, and when the amplitude of said negative EMG envelope waveform falls within said predetermined motor window for said predetermined motor window period.

13. A method of detecting an epileptic seizure in a person comprising the steps of:
   (a) monitoring the amount of brain activity of said person to produce a brain activity signal;
   (b) sampling said brain activity signal at a sampling frequency to produce a brain activity signal amplitude;
   (c) incrementing a brain activity counter when said brain activity signal amplitude is within a predetermined brain window and decrementing said brain activity counter when said brain activity signal is without said predetermined brain window; and
   (e) indicating that an epileptic seizure is occurring when said brain activity counter is above a brain threshold.

14. The method of claim 13 wherein the step of monitoring the brain activity of said person is done by means of an electroencephalograph (EEG) and brain activity signal is an EEG waveform.

15. The method of claim 14 wherein said EEG waveform has a positive EEG component and a negative EEG component, wherein said step of sampling is acted upon said positive EEG component and said negative EEG component, further wherein said brain activity counter includes a positive brain activity counter and a negative brain activity counter, the method further including the step of:
   (a) integrating said positive EEG component to provide a positive EEG envelope waveform and integrating said negative EEG component to provide a negative EEG envelope waveform;
   (b) incrementing said positive brain activity counter when said positive EEG envelope waveform is within said predetermined brain window and decrementing said positive brain activity counter when said positive EEG envelope waveform is without said predetermined brain window, and
   (c) incrementing said negative brain activity counter when said negative EEG envelope waveform is within said predetermined brain window and decrementing said negative brain activity counter when said negative EEG envelope waveform is without said predetermined brain window.

16. A method of detecting an epileptic seizure in a person comprising the steps of:
   (a) monitoring the amount of motor activity of said person as a motor activity signal;
   (b) sampling said motor activity signal at a sampling frequency to produce a motor activity signal amplitude;
   (c) incrementing a motor activity counter when said motor activity signal amplitude is within a predetermined motor window and decrementing said motor activity counter when said motor activity signal is without said predetermined motor window; and
   (e) indicating that an epileptic seizure is occurring when said motor activity counter is above a motor threshold.

17. The method of claim 16 wherein the step of monitoring the brain activity of said person is done by means of an electromyograph (EMG) and said motor activity signal is an EMG waveform.

18. The method of claim 17 wherein said EMG waveform has a positive EMG component and a negative EMG component, wherein said step of sampling is acted upon said positive EMG component and said negative EMG component, further wherein said motor activity counter includes a positive motor activity counter and a negative motor activity counter, the method further including the step of:
   (a) integrating said positive EMG component to provide a positive EMG envelope waveform and integrating said negative EMG component to provide a negative EMG envelope waveform;
   (b) incrementing said positive motor activity counter when said positive EMG envelope waveform is within said predetermined motor window and decrementing said positive motor activity counter when said positive EMG envelope waveform is without said predetermined motor window; and
   (c) incrementing said negative motor activity counter when said negative EMG envelope waveform is within said predetermined motor window and decrementing said negative motor activity counter when said negative EMG envelope waveform is without said predetermined motor window.

19. A method of detecting an epileptic seizure in a person comprising the steps of:
   (a) monitoring the amount of brain activity of said person as a brain activity signal;

(b) determining if the amplitude of said brain activity signal falls within a predetermined brain window for a predetermined brain window period; and (c) indicating that an epileptic seizure has occurred when said amplitude of said brain activity falls within a predetermined brain window for a predetermined brain window period.

20. The method of claim 19 including wherein the step of monitoring the brain activity of said person is done by means of an electroencephalograph (EEG) and said brain activity signal is an EEG waveform.

21. The method of claim 20 further wherein said EEG waveform has a positive EEG component and a negative EEG component, the method further including the steps of:

(a) integrating said positive EEG component to provide a positive EEG envelope waveform and integrating said negative EEG component to provide a negative EEG envelope waveform;

(b) determining whether the amplitude of said positive EEG envelope waveform falls within said predetermined window for said predetermined brain window period and determining whether the amplitude of said negative EEG envelope waveform falls within said predetermined brain window for said predetermined brain window period; and (c) indicating that an epileptic seizure has occurred when said amplitude of said positive EEG envelope waveform falls within said predetermined window for said predetermined brain window period and when the amplitude of said negative EEG envelope waveform falls within said predetermined brain window for said predetermined brain window period.

22. A method of detecting an epileptic seizure in a person comprising the steps of:

(a) monitoring the amount of motor activity of said person as a motor activity signal;

(b) determining if the amplitude of said motor activity signal falls within a predetermined motor window for a predetermined motor window period; and (c) indicating that an epileptic seizure has occurred when said amplitude of said motor activity signal falls within a predetermined motor window for a predetermined motor window period.

23. The method of claim 22 including wherein the step of monitoring the brain activity of said person is done by means of an electromyograph (EMG) and said motor activity signal is an EMG waveform.

24. The method of claim 23 further wherein said EMG waveform has a positive EMG component and a negative EMG component, the method further including the steps of:

integrating said positive EMG component to provide a positive EMG envelope waveform and integrating said negative EMG component to provide a negative EMG envelope waveform;

determining whether the amplitude of said positive EMG envelope waveform falls within said predetermined window for said predetermined motor window time and determining whether the amplitude of said negative EMG envelope waveform falls within said predetermined window for said predetermined motor window period; and indicating that an epileptic seizure has occurred when said amplitude of said positive EMG envelope waveform falls within said predetermined motor window for said predetermined motor window time and when the amplitude of said negative EMG envelope waveform falls within said predetermined motor window for said predetermined motor window period.

25. An apparatus for detecting an epileptic seizure in a person comprising:

(a) a brain monitor monitoring the amount of brain activity of said person and producing a brain activity signal;

(b) a motor monitor monitoring the amount of motor activity of said person and producing a motor activity signal;

(c) CPU means for receiving said brain activity signal from said brain monitor and sampling said brain activity signal at a sampling frequency to produce a brain activity signal amplitude and said CPU means for receiving said motor activity signal from said motor monitor and sampling said motor activity signal at said sampling frequency to produce an motor activity signal amplitude, said CPU means also operative to increment a brain activity counter when said brain activity signal amplitude is within said predetermined brain window and decrementing said brain activity counter when said brain activity signal is without said predetermined brain window, said CPU means also operative to increment a motor activity counter when said motor activity signal amplitude is within said predetermined motor window and decrementing said motor activity counter when said motor activity signal is without said predetermined motor window; and (d) output display means, said output display means connected to said CPU means for indicating that an epileptic seizure is occurring when said brain activity counter is above a brain threshold and said motor activity counter is above a motor threshold.

26. The apparatus of claim 25 further including:

means for determining the maximum amplitude of said brain activity signal when said brain activity counter is above said brain threshold; and means for determining the maximum amplitude of said motor activity signal when said motor activity counter is above said motor threshold.

27. The method of claim 25 further including:

means for determining the average amplitude of said brain activity signal over the interval when said brain activity counter is above said brain threshold; and means for determining the average amplitude of said motor activity signal over the interval when said motor activity counter is above said motor threshold.

28. The method of claim 25 further including means for determining the duration of time in which said brain activity counter is above said brain threshold and the said motor activity counter is above said motor threshold.

29. The method of claim 25 wherein said brain monitor is an electroencephalograph (EEG) and said brain activity signal is an EEG waveform and said motor monitor is an electromyograph (EMG) and said motor activity signal is an EMG waveform.

30. The apparatus of claim 29 wherein said EEG waveform has a positive EEG component and a negative EEG component and wherein said EMG waveform has a positive EMG component and a negative EMG component, the apparatus further comprising:

(a) means for integrating said positive EEG component to provide a positive EEG envelope waveform and integrating said negative EEG component to provide a negative EEG envelope waveform;

(b) means for integrating said positive EMG component to provide a positive EMG envelope waveform and integrating said negative EMG component to provide a negative EMG envelope waveform;

wherein said CPU means samples said positive EEG envelope waveform, said negative EEG envelope waveform, said positive EMG envelope waveform, and said negative EMG envelope waveform, further wherein said brain activity counter includes a positive brain activity counter and a negative brain activity counter, said positive brain activity counter being incremented when said positive EEG envelope waveform is within said predetermined brain window and decremented when said positive EEG envelope waveform is without said predetermined brain window, said negative brain activity counter being incremented when said negative EEG envelope waveform is within said predetermined brain window and decremented when said negative EEG envelope waveform is without said predetermined brain window; and further wherein said motor activity counter includes a positive motor activity counter and a negative motor activity counter, said positive motor activity counter being incremented when said positive EMG envelope waveform is within said predetermined motor window and decremented when said positive EMG envelope waveform is without said predetermined motor window, said negative motor activity counter being incremented when said negative EMG envelope waveform is within said predetermined motor window and decremented when said negative EMG envelope waveform is without said predetermined motor window.

* * * * *

UNITED STATES PATENT AND TRADEMARK OFFICE
CERTIFICATE OF CORRECTION

PATENT NO. : 5,349,962          Page 1 of 2

DATED : September 27, 1994

INVENTOR(S) : J.S. Lockard et al.

It is certified that error appears in the above-identified patent and that said Letters Patent is hereby corrected as shown below:

| COLUMN | LINE | |
|---|---|---|
| 1 | 10 | After "human." and before "BACKGROUND" insert new paragraph as follows: "This invention was made with government support under NIH research contract NO1-NS-1-2282 and NIH research grant NS-04053 awarded by the National Institutes of Health. The government has certain rights in the invention." |
| 1 | 58 | "memory. (RAM)," should read -- nemory (RAM)-- |
| 3 | 46 | "pans" should read --parts-- |
| 4 | 5 | "fore" should read --form-- |
| 11 (Claim 1, | 8 Line 21) | "without said" should read --without a-- |
| 14 (Claim 18, | 48 Line 8) | "the step of:" should read --the steps of:-- |
| 15 (Claim 19, | 5 Line 9) | "brain activity falls" should read --brain activity signal falls-- |

UNITED STATES PATENT AND TRADEMARK OFFICE
CERTIFICATE OF CORRECTION

PATENT NO. : 5,349,962
DATED : September 27, 1994
INVENTOR(S) : J.S. Lockard, et. al.

It is certified that error appears in the above-indentified patent and that said Letters Patent is hereby corrected as shown below:

```
   16         19          "Produce an" should read --produce a--
(Claim 25,  Line 15)
```

Signed and Sealed this

Twenty-fourth Day of January, 1995

Attest:

BRUCE LEHMAN

*Attesting Officer*        *Commissioner of Patents and Trademarks*

UNITED STATES PATENT AND TRADEMARK OFFICE
CERTIFICATE OF CORRECTION

PATENT NO. : 5,349,962
DATED : September 27, 1994
INVENTOR(S) : J.S. Lockard et al.

It is certified that error appears in the above-identified patent and that said Letters Patent is hereby corrected as shown below:

| COLUMN | LINE | |
|---|---|---|
| 13 (Claim 13, | 58 line 13) | "(e)" should read --(d)-- |
| 14 (Claim 16, | 34 line 14) | "(e)" should read --(d)-- |
| 14 (Claim 17, | 38 line 2) | "brain" should read --motor-- |
| 15 (Claim 23, | 47 line 2) | "brain" should read --motor-- |
| 16 (Claim 27, | 45 line 1) | "method" should read --apparatus-- |
| 16 (Claim 28, | 54 line 1) | "method" should read --apparatus-- |
| 16 (Claim 29, | 59 line 1) | "method" should read --apparatus-- |

Signed and Sealed this

Twenty-second Day of December, 1998

Attest:

BRUCE LEHMAN

*Attesting Officer*    Commissioner of Patents and Trademarks